United States Patent
Baum et al.

(10) Patent No.: US 6,623,656 B2
(45) Date of Patent: Sep. 23, 2003

(54) SOURCE REAGENT COMPOSITION FOR CVD FORMATION OF ZR/HF DOPED GATE DIELECTRIC AND HIGH DIELECTRIC CONSTANT METAL OXIDE THIN FILMS AND METHOD OF USING SAME

(75) Inventors: Thomas H. Baum, New Fairfield, CT (US); Chongying Xu, New Milford, CT (US); Witold Paw, New Fairfield, CT (US); Bryan C. Hendrix, Danbury, CT (US); Jeffrey F. Roeder, Brookfield, CT (US); Ziyun Wang, New Milford, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 49 days.

(21) Appl. No.: 09/793,023

(22) Filed: Feb. 26, 2001

(65) Prior Publication Data

US 2002/0132048 A1 Sep. 19, 2002
(Under 37 CFR 1.47)

Related U.S. Application Data

(63) Continuation-in-part of application No. 09/414,133, filed on Oct. 7, 1999, now Pat. No. 6,399,208.

(51) Int. Cl.⁷ .......................... C23C 16/40; C23C 16/18; C23C 16/46; C09K 3/00; C08J 3/02; B32B 9/00

(52) U.S. Cl. .......................... 252/62.9 PZ; 252/62.9 R; 252/518.1; 252/182.1; 556/51; 556/54; 428/470; 428/689; 427/255.28; 106/287.19; 423/69; 423/608

(58) Field of Search .................... 428/470, 689; 427/255.28, 255.6; 106/1.12, 1.22; 423/69, 608; 252/62.9 PZ, 518.1; 556/51, 54

(56) References Cited

U.S. PATENT DOCUMENTS

| | | |
|---|---|---|
| 5,204,314 A | 4/1993 | Kirlin et al. |
| 5,225,561 A | 7/1993 | Kirlin et al. |
| 5,280,012 A | 1/1994 | Kirlin et al. |
| 5,342,648 A | 8/1994 | MacKenzie |
| 5,453,494 A | 9/1995 | Kirlin et al. |
| 5,536,323 A | 7/1996 | Kirlin et al. |
| 5,677,002 A | 10/1997 | Kirlin et al. |
| 5,820,664 A | * 10/1998 | Gardiner et al. ........ 106/287.17 |
| 5,840,897 A | 11/1998 | Kirlin et al. |
| 5,859,274 A | 1/1999 | Baum et al. |
| 5,916,359 A | 6/1999 | Baum et al. |
| 5,919,522 A | 7/1999 | Baum et al. |
| 6,063,639 A | 5/2000 | Kim et al. |
| 6,080,593 A | 6/2000 | Kim et al. |
| 6,110,529 A | 8/2000 | Gardiner et al. |
| 6,190,991 B1 | 2/2001 | Beitel et al. |

FOREIGN PATENT DOCUMENTS

| | | | |
|---|---|---|---|
| EP | 92756 | * 11/1983 | ............. C07F/7/00 |
| JP | 05013676 | 1/1993 | |
| WO | WO 9318202 | * 9/1993 | ............. C23C/16/18 |
| WO | WO 9851837 | * 11/1998 | ............. B05D/3/02 |

OTHER PUBLICATIONS

Gan, J.–Y. et al., "Dielectric property of $(TiO_2)_x$–$(Ta_2O_5)_{1-x}$ thin films," Appl. Phys. Lett. 72 (3), p. 332 Jan. 19, 1998.
Alers, G. B. et al., "Nitrogen plasma annealing for low temperature $Ta_2O_5$ films" Appl. Phys. Lett. 72 (11), p. 1308, Mar. 16, 1998.

(List continued on next page.)

Primary Examiner—Mark Kopec
Assistant Examiner—Kallambella Vijayakumar
(74) Attorney, Agent, or Firm—Margaret Chappuis

(57) ABSTRACT

Chemical vapor deposition (CVD) precursor compositions for forming Zr/Hf doped gate dielectric, ferroelectric, or high dielectric constant (k) metal oxide thin films. The precursor composition in one embodiment comprises a metal precursor having a general formula M(β-diketonate)$_2$(OR)$_2$, wherein M is Zr or Hf, and R is t-butyl. The precursor composition may also comprise a solvent medium selected from the group consisting of ethers, glymes, tetraglymes, amines, polyamines, alcohols, glycols, aliphatic hydrocarbon solvents, aromatic hydrocarbon solvents, cyclic ethers, and compatible combinations of two or more of the foregoing.

45 Claims, 13 Drawing Sheets

OTHER PUBLICATIONS

Kirlin et al., "MOCVD of BaSrTiO$_3$ for ULSI DRAMS", Integrated Ferroelectrics vol. 7, p. 307, 1995.

Van Dover, R.B., "Amorphous lanthanide–doped TiO$_x$ dielectric films", Appl. Phys. Lett. 74 (20) p. 3041, May 17, 1999.

Roy, P. K., et al., "Stacked high–ϵ gate dielectric for giga–scale integration of metal–oxide–semiconductor technologies" Appl. Phys. Lett. 72 (22) p. 2835, Jun. 1, 1998.

Van Dover, R.B. et al., "Discovery of a useful thin–film dielectric using a composition–spread approach", Nature, vol. 392, Mar. 12, 1998, p. 162.

Nomura, Koji et al., "Electrical properties of Al$_2$O$_3$–Ta$_2$O$_5$ composite dielectric thin films prepared by RF reactive sputtering", Solid State Tech., Apr. 1997, p. 922.

Alers, G.B. et al., "Advanced amorphous dielectrics for embedded capacitors", IEDM, 99–797, p. 33.3.1.

Kawano, H., et al, "Effects of crystallization on structural and dielectric properties of thin amorphous films of (1–x)BaTiO$_3$–xSrTiO$_3$ (x=0–0.5, 1.0), "J. Appl. Phys., 73 (10), May 15, 1993, p. 5141.

Van Dover, R.B. et al., "Advanced dielectrics for gate oxide, DRAM and rf capacitors", IDEM 98–823, p 30.6.1.

U.S. patent application Ser. No. 09/414,133, Thomas H. Baum et al., filed Oct. 7, 1999.

Inorganic Chemistry, 1999, vol. 38, pp. 1432–1437.

Jones, et al., "MOCVD of Zirconia Thin Films by Direct Liquid Injection Using a New Class of Zirconium Precursor", Chem. Vap. Dep., vol. 4, 1998, pp. 46–49.

* cited by examiner

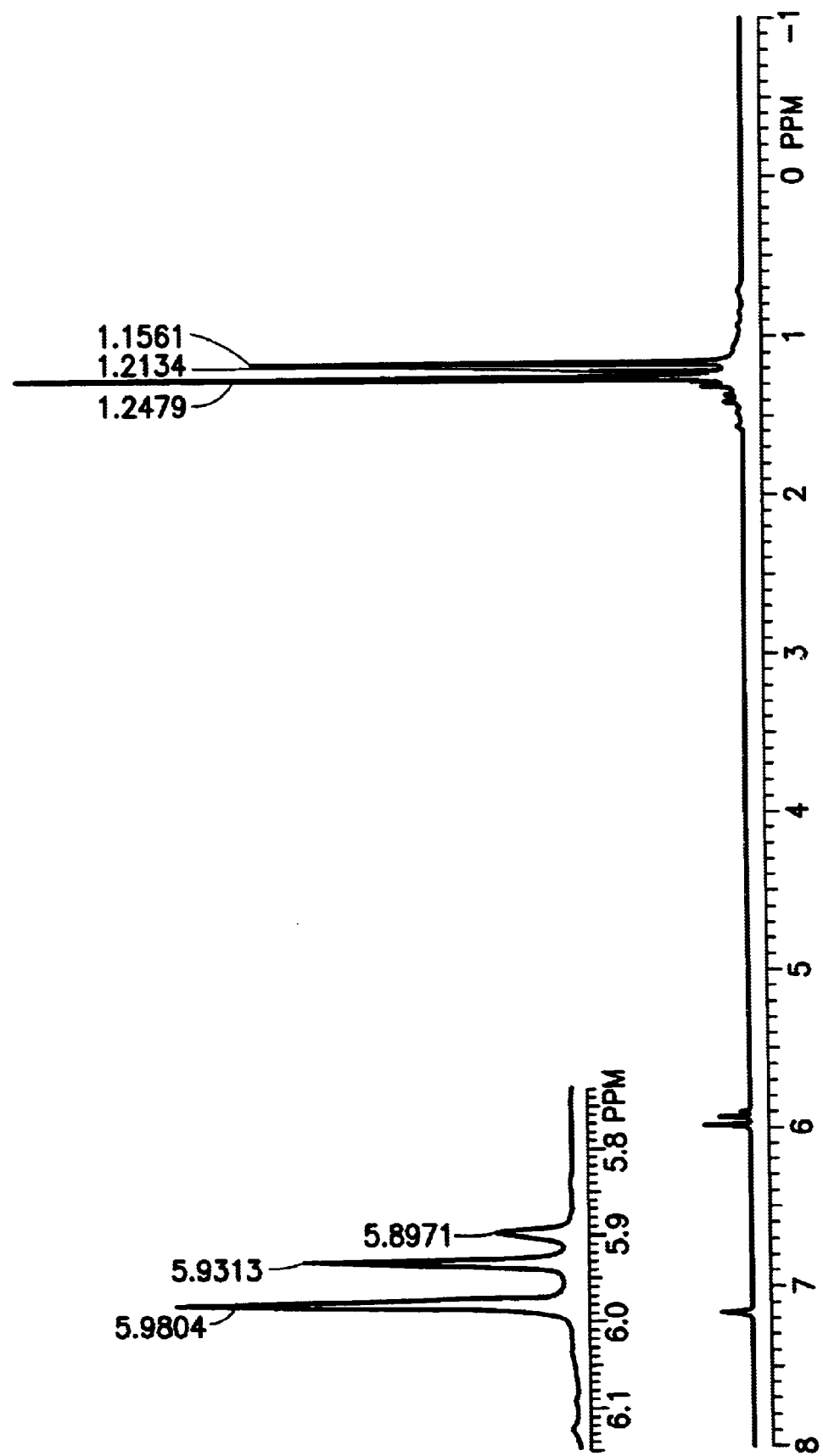

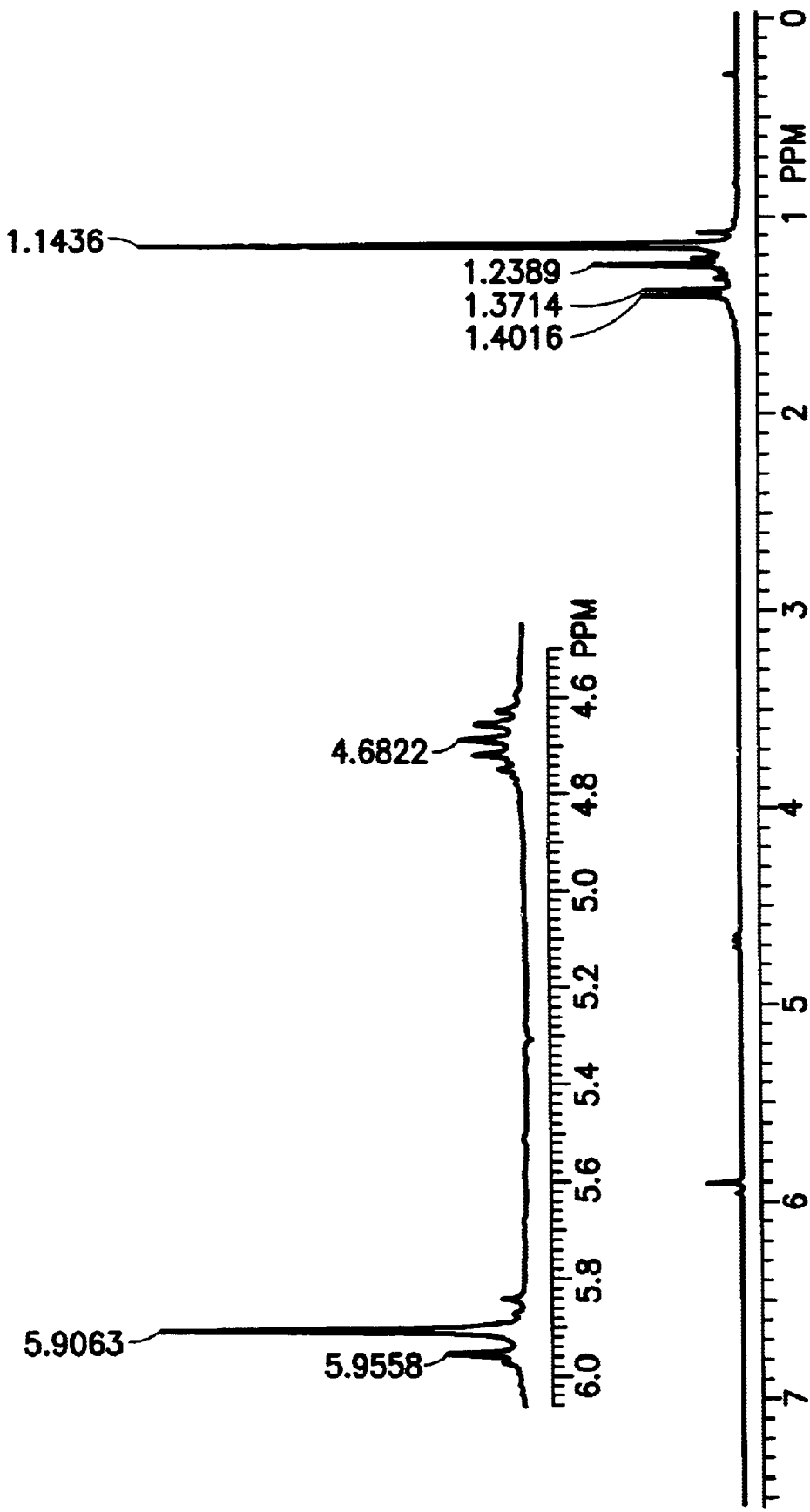

SOURCE REAGENT COMPOSITION FOR CVD FORMATION OF ZR/HF DOPED GATE DIELECTRIC AND HIGH DIELECTRIC CONSTANT METAL OXIDE THIN FILMS AND METHOD OF USING SAME

CROSS-REFERENCE TO RELATED APPLICATIONS

This is a continuation-in-part of U.S. patent application Ser. No. 09/414,133 filed Oct. 7, 1999, now U.S. Pat. No. 6,399,208.

BACKGROUND OF THE INVENTION

1. Filed of the Invention

The present invention relates to zirconium and hafnium metal precursors useful for chemical vapor deposition (CVD) of Zr/Hf doped gate dielectric, high dielectric constant (k) and/or ferroelectric metal oxide thin films.

2. Description of the Related Art

Zirconium and hafnium-containing silicates possess dielectric constant (k) values in the range of from about 10 to 15, and therefore are highly useful as gate dielectric materials in various microelectronic structures and devices. Zirconium- and hafnium-doped ferroelectric or high dielectric constant complex metal oxides, such as $Pb(Zr,Ti)O_3$, are also being considered for the manufacturing of microelectronic devices.

In such applications, the choice of zirconium or hafnium source reagents is of critical importance for the successful chemical vapor deposition of high quality Zr/Hf-doped gate dielectric or high dielectric constant metal oxide thin films.

Fabrication of high quality Zr/Hf doped gate dielectric, high dielectric constant and/or ferroelectric metal oxide thin films requires that the zirconium or hafnium CVD source reagents so employed produce a clean interface between the substrate surface and the Zr/Hf thin films deposited thereon. Deleterious occurrence of side reactions, e.g., when the substrate is silicon, produce predominantly silicon dioxide ($SiO_2$), locally doped $SiO_2$, and/or other surface impurities, are desirably minimized, because formation of such surface impurities reduces the capacitance and therefore compromises performance of the deposited gate dielectric, high dielectric constant and/or ferroelectric metal oxide thin films.

Further, the Zr/Hf source reagents must be thermally stable to avoid premature decomposition of such source reagents before they reach the CVD reaction chamber during the CVD process. Premature decomposition of source reagents not only results in undesirable accumulation of side products that will clog fluid flow conduits of the CVD apparatus, but also causes undesirable variations in composition of the deposited gate dielectric, high dielectric constant and/or ferroelectric metal oxide thin film.

Moreover, the Zr/Hf source reagents have to be chemically compatible with other source reagents used in the CVD process. "Chemically compatible" means that the Zr/Hf source reagents will not undergo undesirable side reactions with other source reagents, e.g., reagents containing silicon or other metals, such as Pb and/or Ti.

Finally, the Zr/Hf source reagents must be able to maintain their chemical identity over time when dissolved or suspended in organic solvents. Any change in chemical identity of source reagents in the solvent medium is deleterious since it impairs the ability of the CVD process to achieve repeatable delivery and film growth.

There is a continuing need in the art to provide improved Zr/Hf source reagents suitable for high efficiency CVD processes, for fabricating corresponding high quality Zr/Hf-doped gate dielectric, high dielectric constant and/or ferroelectric metal oxide thin films.

SUMMARY OF THE INVENTION

The present invention broadly relates to a Zr/Hf source reagent composition having utility for forming dielectric thin films such as doped gate dielectrics, high dielectric constant metal oxides and/or ferroelectric metal oxides, and to a chemical vapor deposition (CVD) method for deposition of Zr or Hf utilizing such composition.

The invention in one aspect relates to a Zr/Hf source reagent composition of the formula:

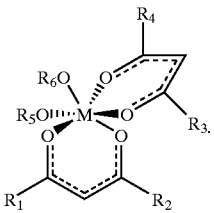

In such formula, M denotes zirconium or hafnium. Each of $R_1$, $R_2$, $R_3$, and $R_4$ is independently selected (i.e., it can either be the same as or different from other(s) of the $R_1$, $R_2$, $R_3$, and $R_4$ substituents) from the group consisting of H, aryl, perfluoroaryl, $C_1-C_8$ alkyl, and $C_1-C_8$ perfluoroalkyl. $R_5$ and $R_6$ are both tert-butyl (tBu).

As used herein, the term "thin film" refers to a material layer having a thickness of less than about 1000 microns.

In a specific aspect of the present invention, the Zr/Hf metal precursor comprises at least one β-diketonate moiety. Illustrative β-diketonate moieties include the following:

| β-diketonate moiety | abbreviation |
| --- | --- |
| 2,4-pentanedione | acac; |
| 1,1,1-trifluoro-2,4-pentanedionato | tfac; |
| 1,1,1,5,5,5-hexafluoro-2,4-pentanedionato | hfac; |
| 2,2,6,6-tetramethyl-3,5-heptanedionato | thd; |
| 2,2,7-trimethyl-3,5-octanedionato | tod; |
| 6,6,7,7,8,8,8-heptafluoro-2,2-dimethyl-3,5-octanedionato | fod. |

One particularly preferred Zr/Hf metal precursor species of the present invention has the formula $M(thd)_2(O-tBu)_2$ wherein M is Zr or Hf. In such precursor, the bulky t-butyl groups function to minimize deleterious isomerization reactions and enhance thermal stability of the precursor. The preferred $M(thd)_2(O-tBu)_2$ precursor can be synthesized by reacting $M(O-tBu)_4$ with two equivalents of Hthd in a dry hydrocarbon or aryl solvent according to the following equation:

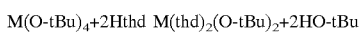

Another aspect of the present invention relates to a CVD source reagent composition comprising a Zr/Hf metal precursor as described hereinabove, and a solvent medium in which the Zr/Hf metal precursor is soluble or suspendable. Providing a source reagent composition in liquid (e.g., solution or suspension) form facilitates rapid volatilization (e.g., flash vaporization) of the source reagent composition and transport of the resultant precursor vapor to a deposition locus such as a CVD reaction chamber. Further, when used in solution the precursor stability is greatly improved over other prior art alcoxide analogs.

The solvent medium utilized in the CVD source reagent composition may comprise any suitable solvent species, or combination of solvent species, with which the metal precursor(s) are compatible. Such solvent medium may for example comprise ethers, glymes, tetraglymes, amines, polyamines, aliphatic hydrocarbon solvents, aromatic hydrocarbon solvents, cyclic ethers, or compatible combinations of two or more of the foregoing solvents.

A particularly preferred solvent species useful in the practice of the present invention is octane.

In yet another aspect, the invention relates to a method of forming a Zr/Hf dielectric thin film on a substrate, wherein the dielectric thin film is selected from the group consisting of doped gate dielectric, high dielectric constant metal oxide and ferroelectric metal oxide, comprising the following steps:

vaporizing a source reagent composition comprising a Zr or Hf metal precursor to form a source reagent precursor vapor;

transporting such source reagent precursor vapor into a chemical vapor deposition zone, optionally using a carrier gas;

contacting the substrate with the source reagent vapor in the chemical vapor deposition zone in the presence of an oxidizer and at elevated temperature, to deposit a corresponding Zr- or Hf-containing thin film on the substrate, e.g., a doped gate dielectric thin film, a high dielectric constant metal oxide thin film and/or a ferroelectric metal oxide thin film;

wherein the Zr or Hf metal precursor has the following formula:

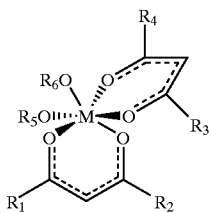

wherein:
M is Zr or Hf;
each of $R_1$, $R_2$, $R_3$, and $R_4$ is independently selected from the group consisting of H, aryl, perfluoroaryl, $C_1$–$C_8$ alkyl, and $C_1$–$C_8$ perfluoroalkyl; and
$R_5$ and $R_6$ are both t-butyl groups.

The step of vaporizing the source reagent composition comprising the Zr/Hf metal precursor is preferably carried out at a vaporization temperature in the range of from about 100° C. to about 300° C. Within this narrow range of vaporization temperature, the Zr/Hf metal precursor is effectively vaporized with a minimum extent of premature decomposition.

In the optional use of a carrier gas in the practice of the present invention, for transporting the vaporized source reagent composition into the chemical vapor deposition zone, suitable carrier gas species include gases that do not adversely affect the metal-containing film being formed on the substrate. Preferred gases include argon, helium, krypton or other inert gas, with argon gas generally being most preferred. In one illustrative embodiment, argon gas may be introduced for mixing with the vaporized source reagent composition at a flow rate of about 100 standard cubic centimeters per minute (sccm).

Oxidizers useful for the broad practice of the present invention include, but are not limited to, $O_2$, $N_2O$, and $O_3$. More preferably, the oxidizer used comprises oxygen, and in one illustrative embodiment corresponding to the argon flow rate illustratively described above, oxygen is introduced into the chemical vapor deposition zone at a flow rate of about 700 sccm.

The deposition of the Zr/Hf-containing dielectric thin film is preferably carried out under an elevated deposition temperature in a range of from about 300° C. to about 750° C.

Other aspects, features, and embodiments of the invention will be more fully apparent from the ensuing disclosure and appended claims.

BRIEF DESCRIPTION OF THE DRAWINGS

FIGS. 4a–4c are nuclear magnetic resonance (NMR) spectra of $Zr(thd)_2(O-iPr)_2$ in $C_6D_6$ showing cis- and trans-isomers equilibration over time.

FIGS. 5a–5c are nuclear magnetic resonance (NMR) spectra of $Hf(thd)_2(O-iPr)_2$ in $C_6D_6$ showing cis- and trans-isomers equilibration over time.

DETAILED DESCRIPTION OF THE INVENTION AND PREFERRED EMBODIMENTS THEREOF

Figure 1:
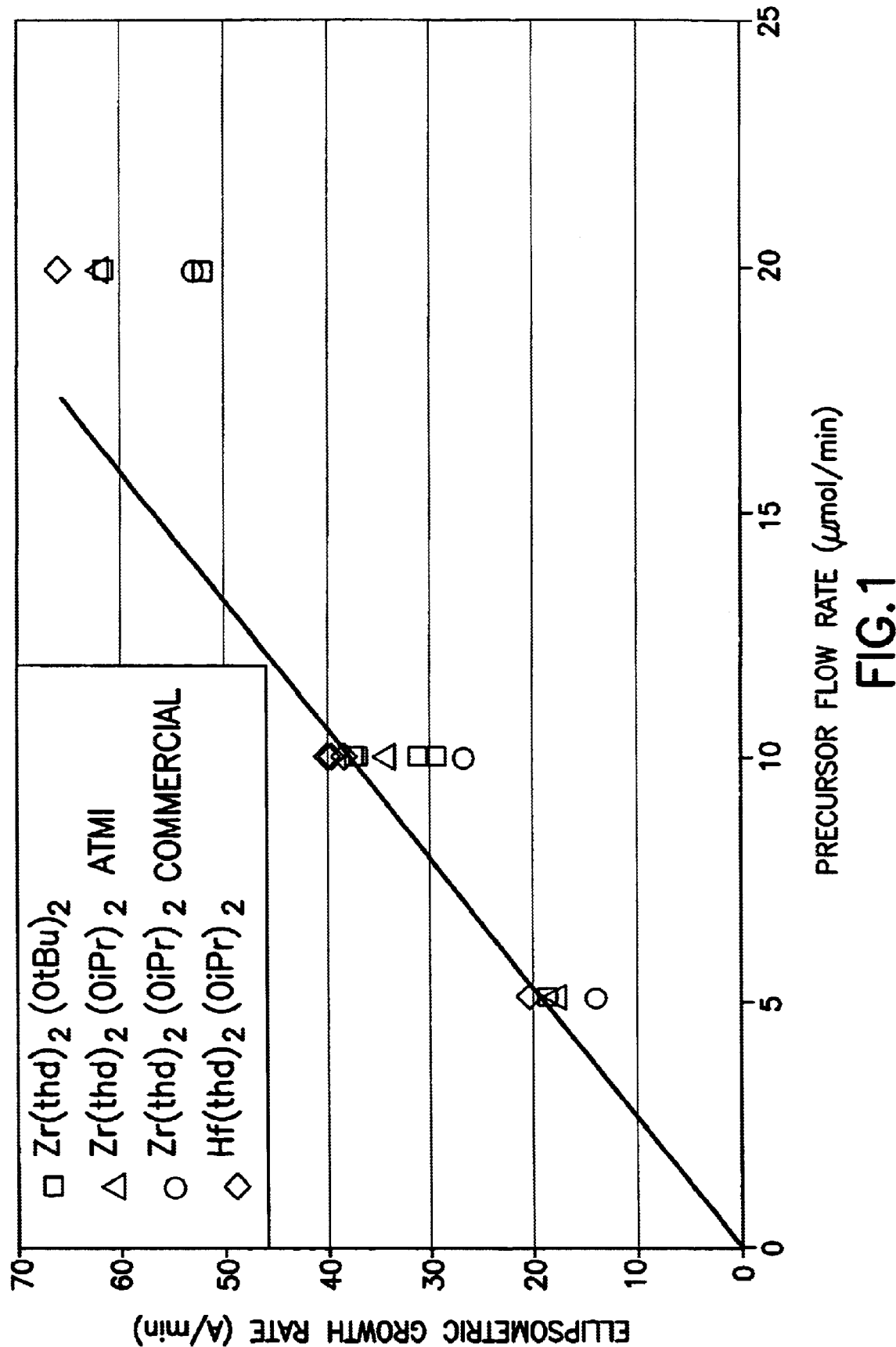
FIG. 1 is a comparative plot of film growth rates calculated from ellipsometric measurements, as a function of precursor flow rate, for various Zr or Hf metal precursors.

The disclosure of the following commonly owned United States patents are hereby incorporated herein by reference in their respective entireties:

U.S. patent application Ser. No. 09/414,133 filed Oct. 7, 1999 in the names of Thomas H. Baum, et al. and issued Jun. 4, 2002 as U.S. Pat. No. 6,399,208;

U.S. patent application Ser. No. 08/835,768 filed Apr. 8, 1997 in the names of Thomas H. Baum, et al., and issued Jul. 6, 1999 as U.S. Pat. No. 5,919,522;

U.S. patent application Ser. No. 08/484,654 filed Jun. 7, 1995 in the names of Robin A. Gardiner et al., and issued Aug. 29, 2000 as U.S. Pat. No. 6,110,529;

U.S. patent application Ser. No. 08/414,504 filed Mar. 31, 1995 in the names of Robin A. Gardiner et al., and issued Oct. 13, 1998 as U.S. Pat. No. 5,820,664;

U.S. patent application Ser. No. 08/280,143 filed Jul. 25, 1994 in the names of Peter S. Kirlin, et al., and issued Jul. 16, 1996 as U.S. Pat. No. 5,536,323;

U.S. patent application Ser. No. 07/807,807 filed Dec. 13, 1991 in the names of Peter S. Kirlin, et al, and issued Apr. 20, 1993 as U.S. Pat. No. 5,204,314;

U.S. patent application Ser. No. 08/181,800 filed Jan. 15, 1994 in the mines of Peter S. Kirlin, et al., and issued Sep. 26, 1995 as U.S. Pat. No. 5,453,494;

U.S. patent application Ser. No. 07/918,141 filed Jul. 22, 1992 in the names of Peter S. Kirlin, at al., and issued Jan. 18, 1994 as U.S. Pat. No. 5,280,012; and U.S. patent application Ser. No. 07/581,631 filed Sep. 12, 1990 in the names of Peter S. Kirlin, et ml., and issued Jul. 6, 1993 as U.S. Pat. No. 5,225,561.

U.S. patent application Ser. No. 07/918,141 filed Jul. 22, 1992 in the names of (Peter S. Kirlin, at al., and issued Jan. 18, 1994 as U.S. Pat. No. 5,280,012; and U.S. patent application Ser. No. 07/581,631 filed Sep. 12, 1990 in the names of Peter S. Kirlin, et al., and issued Jul. 6, 1993 as U.S. Pat. No. 5,225,561.

The above-identified applications and patents variously describe source reagent compositions and their synthesis and formulations, as well as CVD techniques including liquid delivery CVD, and provide background information with respect to the present invention.

On fundamental grounds, the Zr and Hf compounds of the present invention would not be expected to be suitable for use as advantageous source reagents for depositing Zr and Hf in thin films, e.g., by CVD, since compounds of the general formula $M(thd)_2(O-iPr)_2$ (wherein "thd" denotes 2,2,6,6-tetramethyl-3,5-pentanedionato, and "i-Pr" denotes isopropyl) are known to be highly susceptible to cis- to trans-equilibration, and deleterious proportionation reactions, resulting in an alteration of the chemical identity of such compounds due to formation of dinuclear species, such as $[M(thd)_2(O-iPr)_2]_2$, particularly in organic solvent medium. See INORGANIC CHEMISTRY, 1999, 38, 1432–1437;

In contrast to such expectation, the Zr/Hf source reagent compounds of the invention have been found to be surprisingly stable, even in organic solutions, while at the same time they are volatilizable at low temperatures that are consistent with efficient chemical vapor deposition processing.

The Zr/Hf metalorganic compounds of the present invention have a general formula $M(\beta\text{-diketonate})_2(O\text{-}tBu)_2$. Compounds of such general type have the following structure:

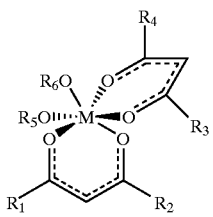

wherein M is Zr or Hf, each of $R_1$, $R_2$, $R_3$, and $R_4$ is independently selected from the group consisting of H, aryl, perfluoroaryl, $C_1$–$C_8$ alkyl, and $C_1$–$C_8$ perfluoroalkyl; and $R_5$ and $R_6$ are both t-butyl groups.

The presence of the bulky t-butyl group in the alkoxide ligands limits the occurrence of cis- to trans-equilibration and eliminates the proportionation to dinuclear species over time, particularly when the compound is in an organic solution or suspension. Such $M(\beta\text{-diketonate})_2(O\text{-}tBu)_2$ compounds are very stable chemically in organic solutions and also possess the following advantageous features: good deposition rates; good thermal stability; higher elemental purity; formation of practically carbon-free films (in contrast to the reported literature, e.g. Jones, et al., "MOCVD of Zirconia Thin Films by Direct Liquid Injection Using a New Class of Zirconium Precursor", *Chem. Vap. Dep.*, Vol. 4, 1998, PP. 46–49.); compatibility in solvent media with a variety of other alkoxide/beta-diketonate precursors and/or beta-diketonate precursors for various transition metals and alkali earth metals; ready decomposition at CVD process temperatures; and good solubility in a wide variety of organic solvents and solvent media.

The β-diketonate ligand(s) in the $M(\beta\text{-diketonate})_2(O\text{-}tBu)_2$ compound may be of any suitable type. The β-diketonate ligands in the compound may be the same as or different from one another. Illustrative β-diketonate ligands include the following:

| β-diketonate ligand | abbreviation |
|---|---|
| 2,4-pentanedione | acac; |
| 1,1,1-trifluoro-2,4-pentanedionato | tfac; |
| 1,1,1,5,5,5-hexafluoro-2,4-pentanedionato | hfac; |
| 2,2,6,6-tetramethyl-3,5-heptanedionato | thd; |
| 2,2,7-trimethyl-3,5-octanedionato | tod; |
| 6,6,7,7,8,8,8-heptafluoro-2,2-dimethyl-3,5-octanedionato | fod. |

Particularly preferred β-diketonate ligands of the Zr/Hf source reagent compounds of the invention include 2,2,6,6-tetramethyl-3,5-pentanedionato (thd). $M(thd)_2(O\text{-}tBu)_2$ compounds have high film growth rates and are easily prepared in large quantities and at high purity, as Zr/Hf metal precursors for CVD processes.

Figure 2:
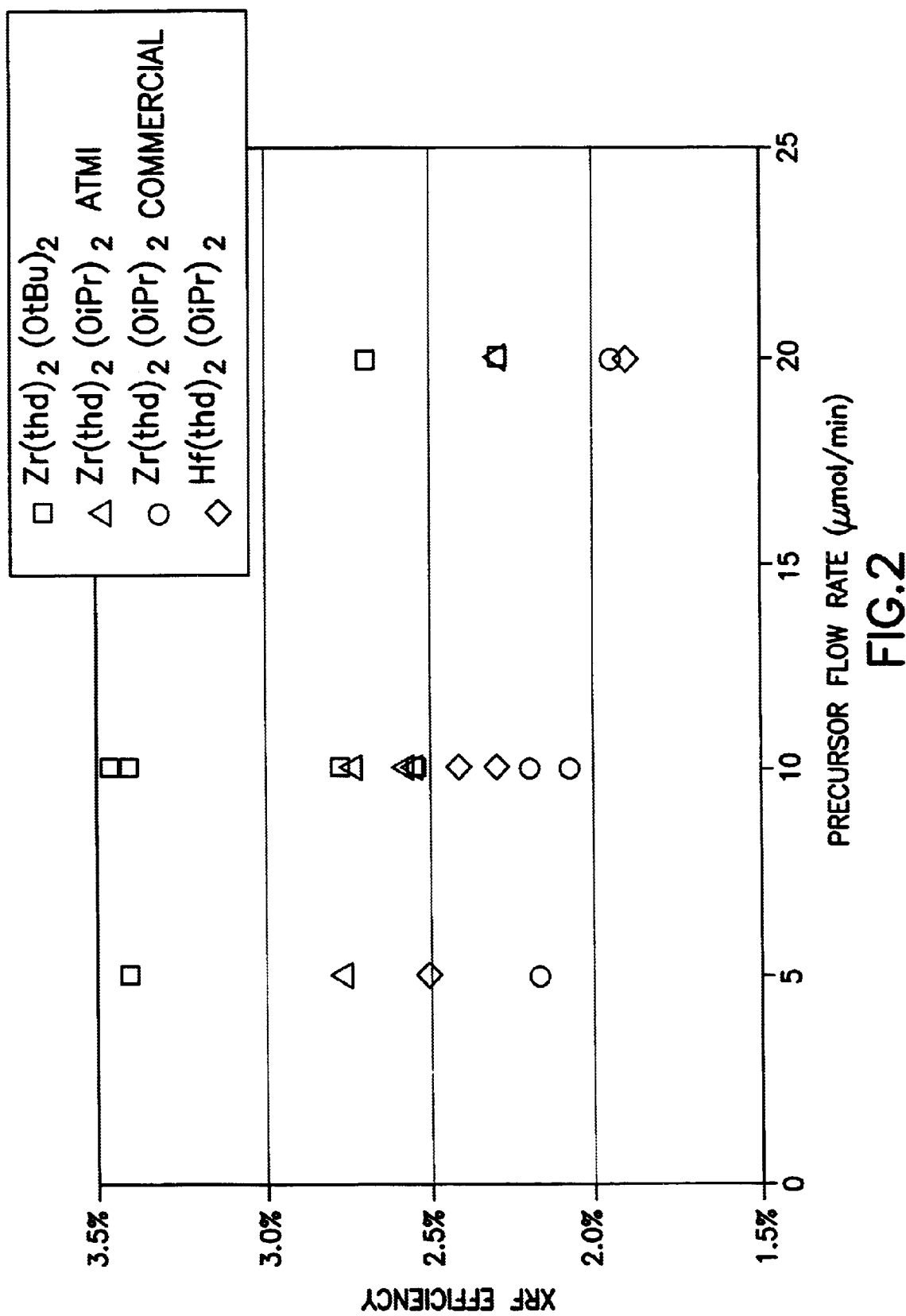
FIG. 2 is a comparative plot of incorporation efficiency of precursors measured using x-ray fluorescence (XRF) technique, as a function of precursor flow rate, for various Zr or Hf metal precursors.

FIGS. 1 and 2 compare film growth rates and efficiency of four metal precursors: $Zr(thd)_2(O\text{-}iPr)_2$ (supplied commercially and labeled as "commercial"), $Zr(thd)_2(O\text{-}iPr)_2$ (synthesized in house at ATMI and labeled "ATMI"), $Zr(thd)_2(O\text{-}tBu)_2$, and $Hf(thd)_2(O\text{-}iPr)_2$. For each precursor, a minimum of five films was grown at three different precursor delivery rates according to the following order: 0.10, 0.05, 0.10, 0.20, and 0.10 ml/min. The film growth time was varied to maintain a constant 100 μmol of precursor delivery amount during each cycle of growth.

In FIG. 1, film thickness of each film so deposited was measured using single-wavelength ellipsometry at 70° C. incidence angle.

In FIG. 2, the film thickness was measured using x-ray fluorescence (XRF). For $ZrO_2$ films, the XRF was calibrated by using the densest films measured by ellipsometry. For $HfO_2$, the XRF was calibrated by assuming that the x-ray efficiencies of such films were equivalent to $TaO_{2.5}$.

FIGS. 1 and 2 show that $Zr(thd)_2(O\text{-}tBu)_2$ has the highest growth rate among the Zr metal precursors.

Figure 3:
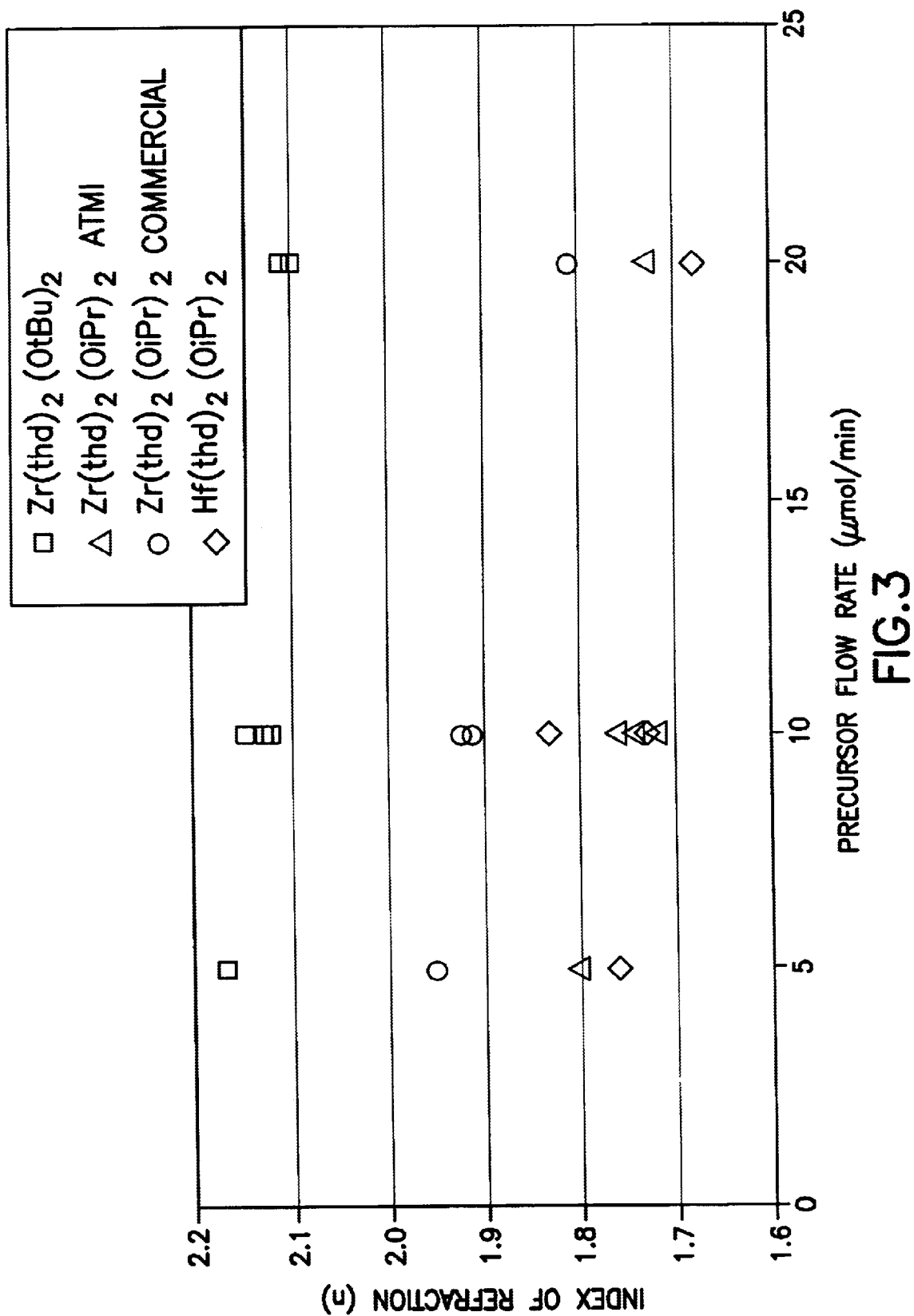
FIG. 3 is a comparative plot of index of refraction measured for various Zr or Hf metal precursors as a function of precursor flow rate.

FIG. 3 compares index of refraction of the same four metal precursors $Zr(thd)_2(O\text{-}iPr)_2$ (commercial), $Zr(thd)_2(O\text{-}iPr)_2$ (ATMI), $Zr(thd)_2(O\text{-}tBu)_2$, and $Hf(thd)_2(O\text{-}iPr)_2$, at similar precursor delivery rates. FIG. 3 shows that $Zr(thd)_2(O\text{-}tBu)_2$ forms the densest $ZrO_2$ film, as indicated by its highest index of refraction.

The composition of $ZrO_2$ films formed by $Zr(thd)_2(O\text{-}iPr)_2$, $Zr(thd)_2(O\text{-}tBu)_2$, and $Hf(thd)_2(O\text{-}tBu)_2$ was analyzed by x-ray photoelectron spectroscopy (XPS) after sputtering the surface layers of the $ZrO_2$ films away to avoid carbon contamination from the ambient. The XPS results show that the carbon levels of films formed using $Zr(thd)_2(O\text{-}tBu)_2$ precursor were below reliable detection range of the XPS. In contrast, carbon levels of films formed by $Zr(thd)_2(O\text{-}iPr)_2$ precursor were above such detection range. This indicates that $Zr(thd)_2(O\text{-}tBu)_2$ is capable of forming carbon-free $ZrO_2$ thin films and reduce carbon contaminants to a lower level than that of films formed by $Zr(thd)_2(O\text{-}iPr)_2$.

The Zr/Hf metal precursors of the invention are usefully employed in a method of forming a Zr/Hf containing dielectric thin film on a substrate, wherein the dielectric thin film is selected from the group consisting of: doped gate dielectric, high dielectric constant metal oxide, and ferroelectric metal oxide.

Such method includes the steps of:

vaporizing a source reagent composition comprising a Zr/Hf metal precursor to form a source reagent vapor;

transporting such source reagent vapor into a chemical vapor deposition zone containing a substrate, optionally using a carrier gas to effect such transport;

contacting the source reagent vapor with a substrate in such chemical vapor deposition zone in the presence of an oxidizer and at elevated temperature to deposit a corresponding Zr- or Hf-containing material on the substrate, e.g., a Zr/Hf doped gate dielectric material, a high dielectric constant and/or ferroelectric metal oxide thin film containing zirconium and/or hafnium;

wherein the Zr/Hf metal precursor has the following formula:

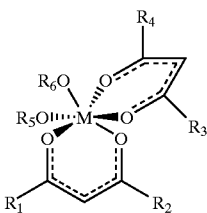

wherein:
M is Zr or Hf;
each of $R_1$, $R_2$, $R_3$, and $R_4$ is independently selected from the group consisting of H, aryl, perfluoroaryl, $C_1-C_8$ alkyl, and $C_1-C_8$ perfluoroalkyl; and
$R_5$ and $R_6$ are both t-butyl groups.

The source reagent composition of the present invention may comprise any suitable solvent medium that is compatible with the metal precursors contained therein. The solvent medium in such respect may comprise a single component solvent, or alternatively a solvent mixture or solution. Illustrative solvent media that may be variously usefully employed include ethers, glymes, tetraglymes, amines, polyamines, aliphatic hydrocarbon solvents, aromatic hydrocarbon solvents, cyclic ethers, and compatible combinations of two or more of the foregoing.

In one preferred embodiment of the present invention, the Zr/Hf metal precursor or precursors are dissolved in octane at a concentration of from about 0.05M to about 0.2 M. In another preferred embodiment, the Zr/Hf metal precursor solution is delivered to vaporization chamber at a delivery rate of from about 0.05 ml/min to about 0.20 ml/min.

The step of vaporizing the source reagent composition containing Zr/Hf metal precursor is preferably carried out at a vaporization temperature in the range from about 100° C. to about 300° C. Within this narrow range of vaporization temperature, the Zr/Hf metal precursor is effectively vaporized with a minimum extent of premature decomposition.

Vaporization of the source reagent composition may be carried out in any suitable manner and using any suitable vaporization means to form corresponding source reagent vapor for contacting with the elevated temperature substrate on which the Zr/Hf doped gate dielectric, high dielectric constant and/or ferroelectric metal oxide thin film is to be formed. The vaporization may for example be carried out with a liquid delivery vaporizer unit of a type as commercially available from Advanced Technology Materials, Inc. (Danbury, Conn.) under the trademark VAPORSOURCE, in which precursor liquid is discharged to a heated vaporization element, such as a porous sintered metal surface, and flash vaporized.

Preferably, a carrier gas is employed in the practice of the present invention for transporting the vaporized source reagent composition into the chemical vapor deposition chamber. Suitable carrier gas species include, without limitation, helium, krypton, argon gas, or other preferably inert gas that does not deleteriously affect the composition, formation or characteristics of the zirconium- or hafnium-containing film being formed on the substrate. By way of example, an argon carrier gas may be employed to form a multicomponent gas stream containing the precursor vapor and the carrier gas. In a specific embodiment, such argon gas may be introduced for mixing with the vaporized source reagent composition at a flow rate of about 100 sccm. Oxidizers useful for the broad practice of the present invention include, but are not limited to, $O_2$, $N_2O$, and $O_3$. Oxygen is a preferred oxidizer species, and in a specific embodiment may be introduced into the chemical vapor deposition chamber at a flow rate of about 700 sccm.

The deposition of the Zr/Hf-doped gate dielectric material or high dielectric constant and or ferroelectric Zr/Hf oxide material is preferably carried out at an elevated deposition temperature in a range of from about 350° C. to about 750° C. The deposition zone may comprise a CVD reactor of any suitable type and conformation, as desirable in a given end use application of the invention.

The features, aspects, and advantages of the present invention are more fully shown with reference to the following non-limiting example.

EXAMPLES

Figure 4A:
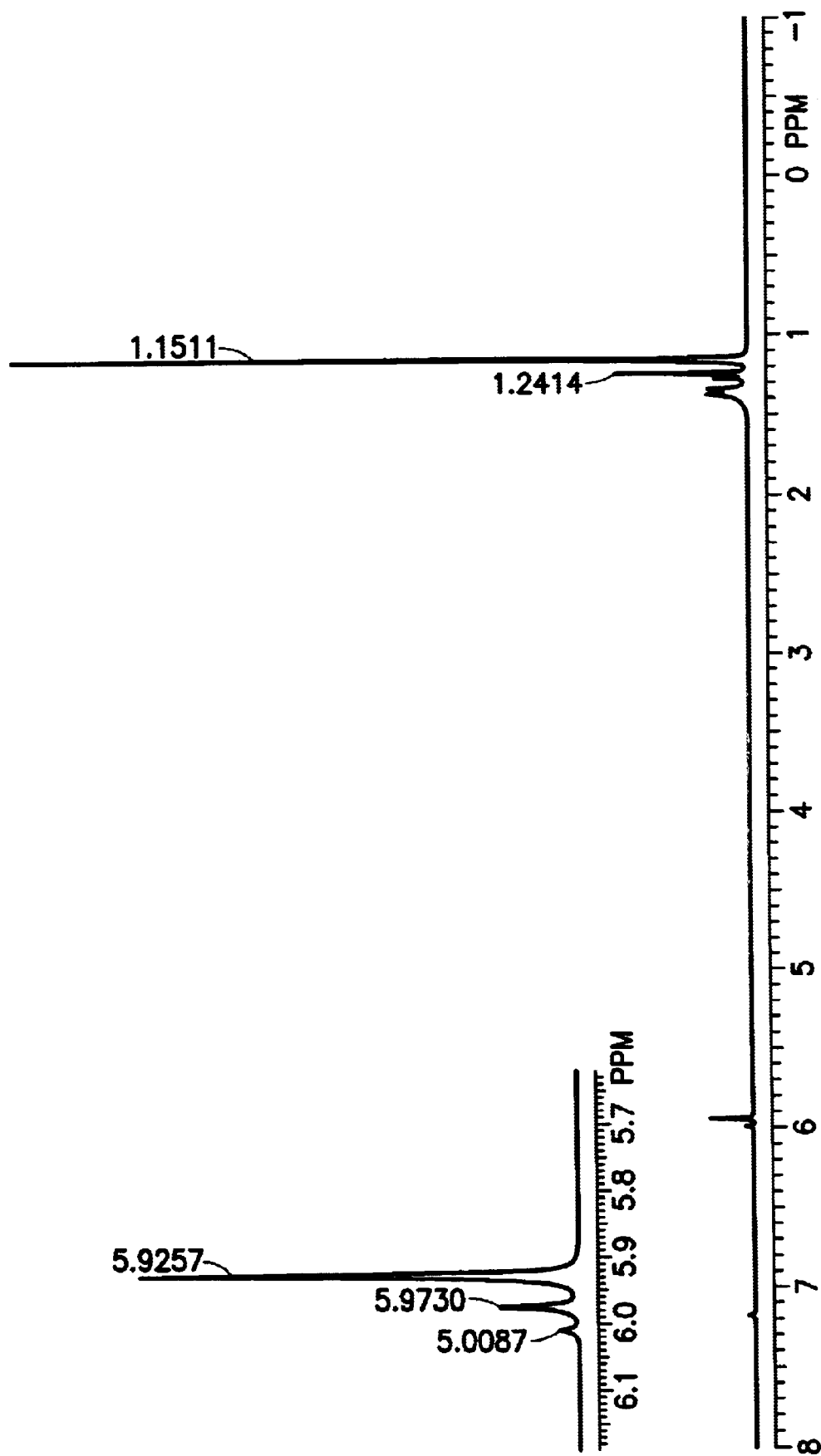
Figure 4B:
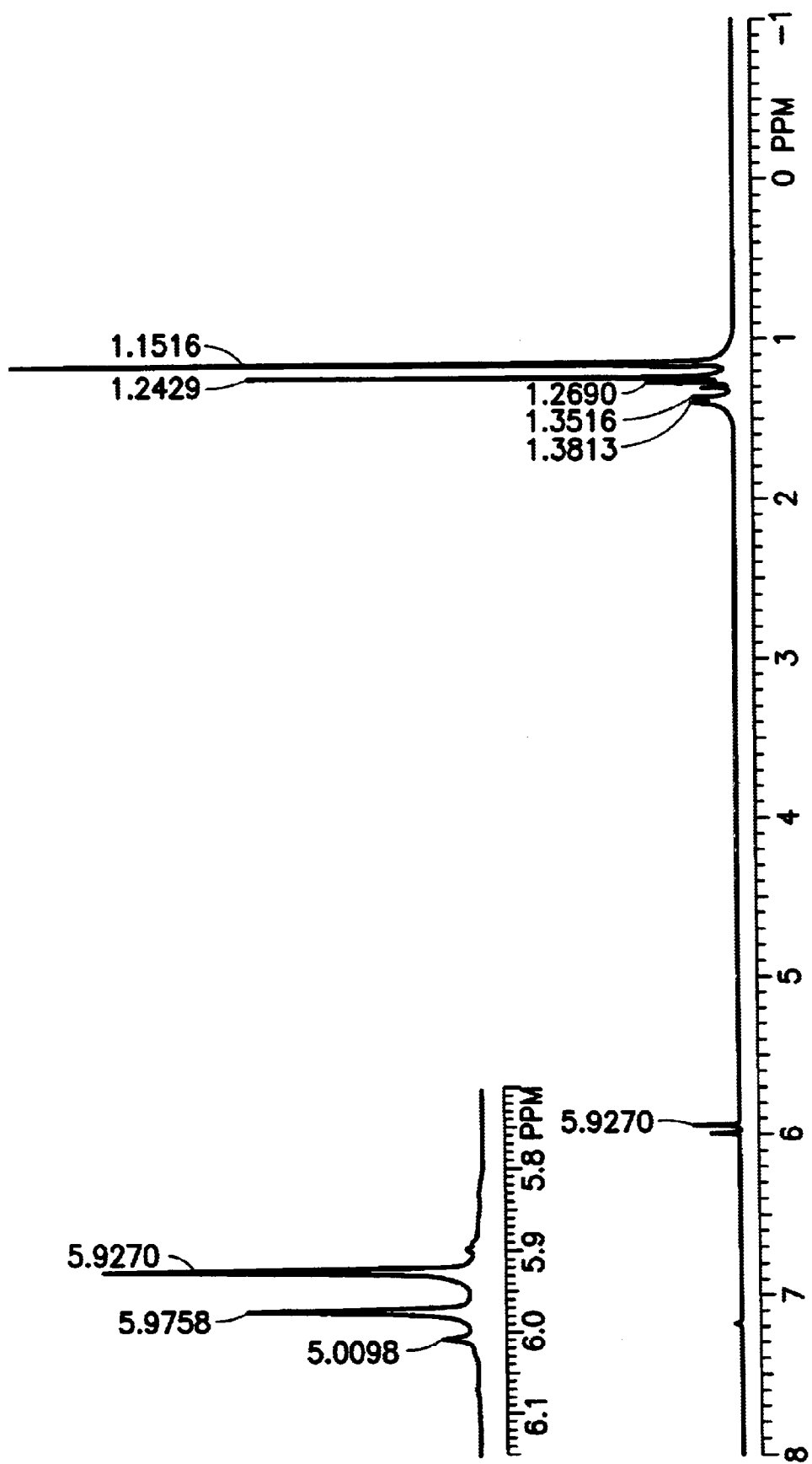

NMR Characterization of Cis- and Trans-Equilibration of $Zr(thd)_2(O-iPr)_2$:

A sample of $Zr(thd)_2(O-iPr)_2$ is dissolved in deuterated benzene solvent. FIGS. 4a–4c, show the $-^1H$ NMR ($C_6D_6$), δ (ppm), spectra of a single sample of $Zr(thd)_2(O-iPr)_2$ over a period of approximately fourteen days. The original sample in FIG. 4a shows the majority of the compound to be in the cis-phase 1.15 (s, 36H=4×—C(C$\underline{H}_3$)$_3$ of thd ligands) and 5.92 (s, 2H=2×C$\underline{H}$ of thd ligands) with a detectable amount of the trans-isomer at 1.24 (s, 36H=4×—C(C$\underline{H}_3$)$_3$ of thd ligands) and 5.97(s, 2H=2×C$\underline{H}$ of thd ligands). FIGS. 4b–4c further evidence the cis- to trans-equilibration of the sample over time as the peaks at 1.24(s, 36H=4×—C(C$\underline{H}_3$)$_3$ of thd ligands) and 5.97(s, 2H=2×C$\underline{H}$ of thd ligands) increase over the fourteen day period (FIG. 4b time lapse=4 days, FIG. 4c time lapse=14 days). Such disproportionation reaction alters the chemical identity of the $Zr(thd)_2(O-iPr)_2$ compound, making it less desirable for CVD applications.

Figure 5A:
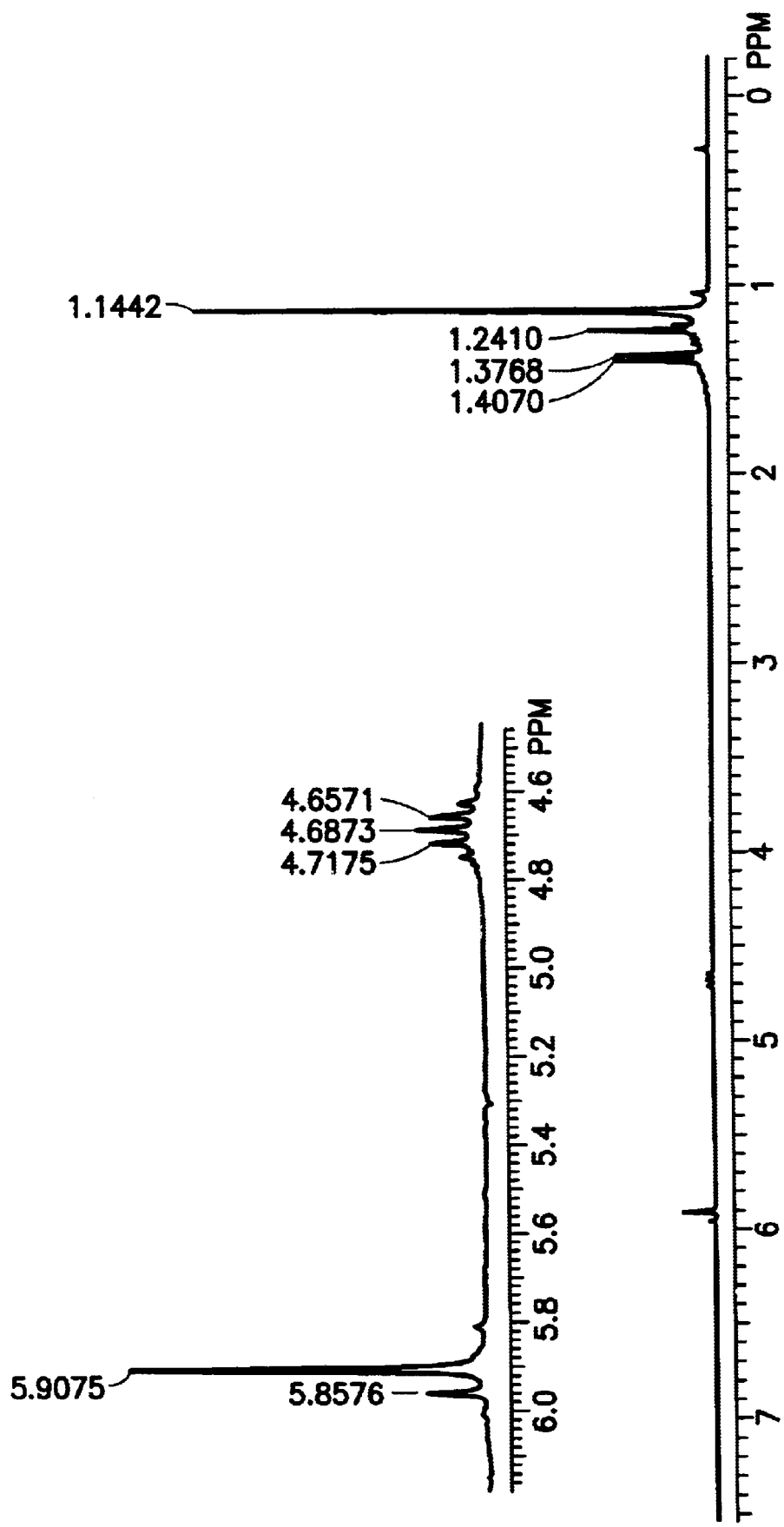
Figure 5C:
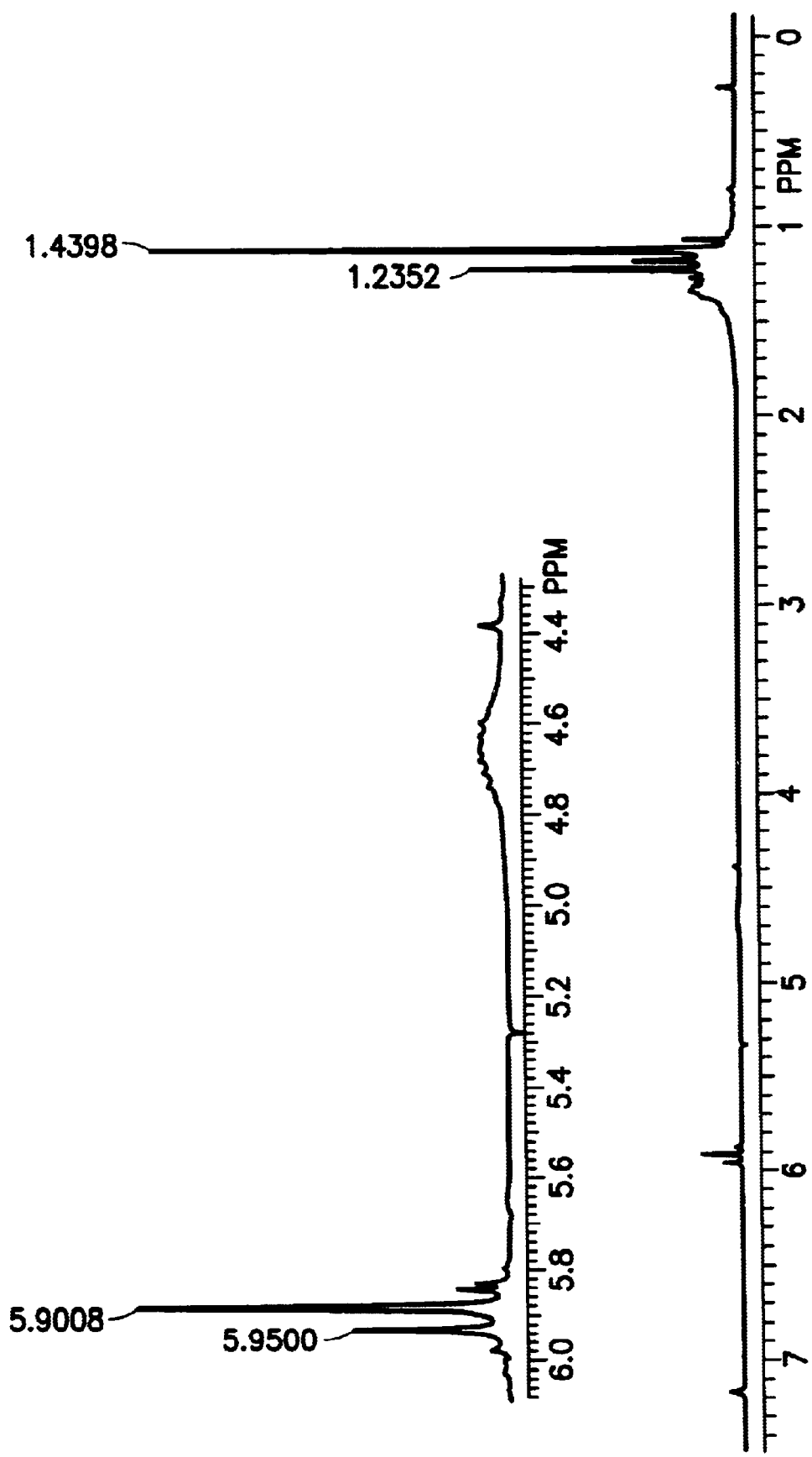

NMR Characterization of Cis- and Trans-Equilibration of $Hf(thd)_2(O-iPr)_2$:

A sample of $Hf(thd)_2(O-iPr)_2$ is dissolved in deuterated benzene solvent. FIGS. 5a–5c, show the $-^1H$ NMR ($C_6D_6$), δ (ppm) spectra of a single sample of $Hf(thd)_2(O-iPr)_2$ over a period of approximately nine days. The original sample in FIG. 5a shows the majority of the compound to be in the cis-phase 1.14 (s, 36H=4×—C(C$\underline{H}_3$)$_3$ of thd ligands) and 5.91 (s, 2H=2×C$\underline{H}$ of thd ligands) with a detectable amount of the trans-isomer at 1.24 (s, 36H=4×—C(C$\underline{H}_3$)$_3$ of thd ligands) and 5.96 (s, 2H=2×C$\underline{H}$ of thd ligands). FIGS. 5b–5c further evidence the cis- to trans-equilibration of the sample over time as the peaks at 1.24 (s, 36H=4×—C(C$\underline{H}_3$)$_3$ of thd ligands) and 5.96 (s, 2H=2×C$\underline{H}$ of thd ligands) increase over the nine day period (FIG. 5b time lapse=24 hours, FIG. 5c time lapse=9 days). Such disproportionation reaction alters the chemical identity of the Hf(thd)$_2$(O-iPr)$_2$ compound, making it less desirable for CVD applications. Such disproportionation reaction alters the chemical identity of the Hf(thd)$_2$(O-iPr)$_2$ compound, making it less desirable for CVD applications.

Figure 6A:
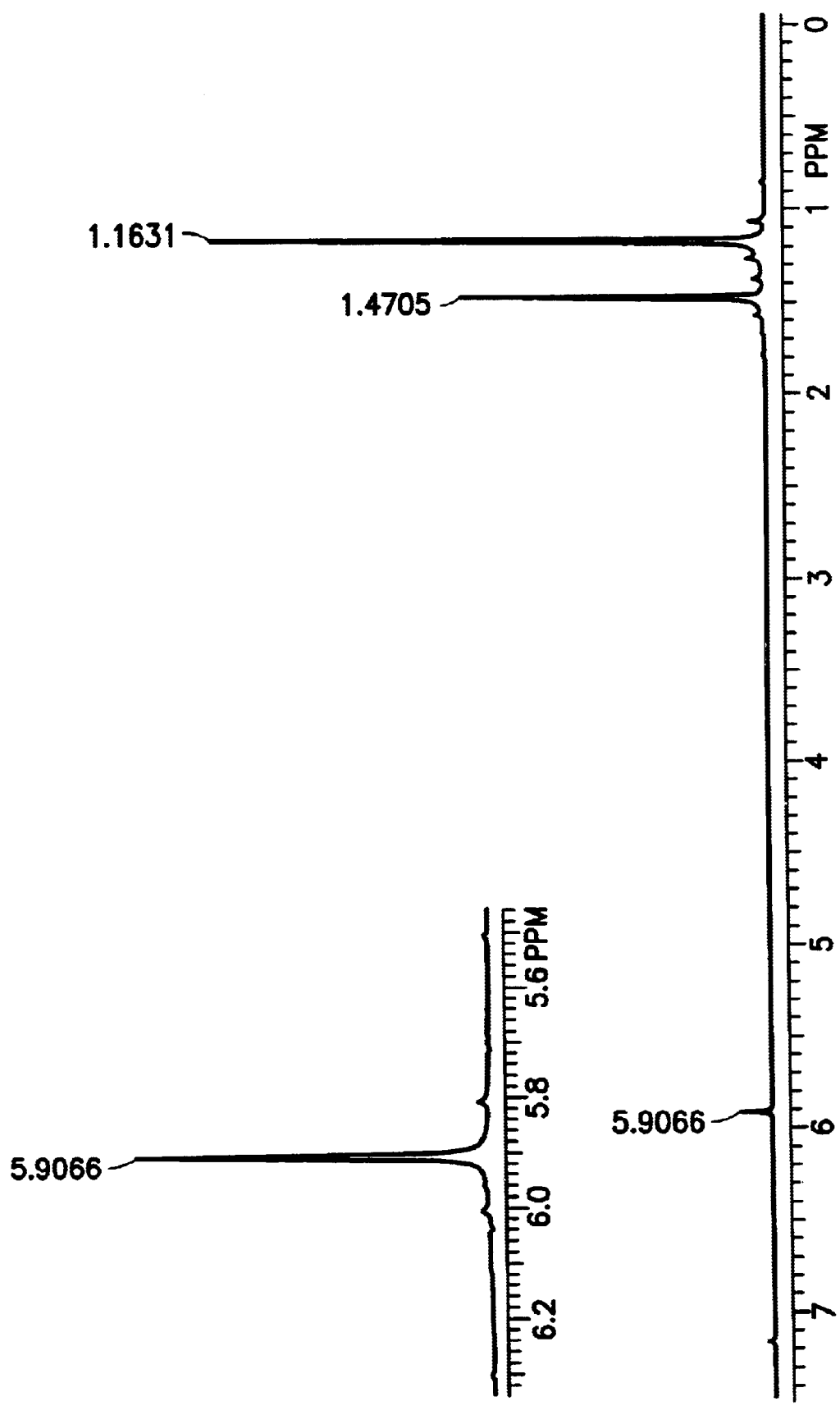
FIGS. 6a–6d are nuclear magnetic resonance (NMR) spectra of $Zr(thd)_2(O-tBu)_2$ in $C_6D_6$ showing no cis- and trans-isomers equilibration over time.
Figure 6B:
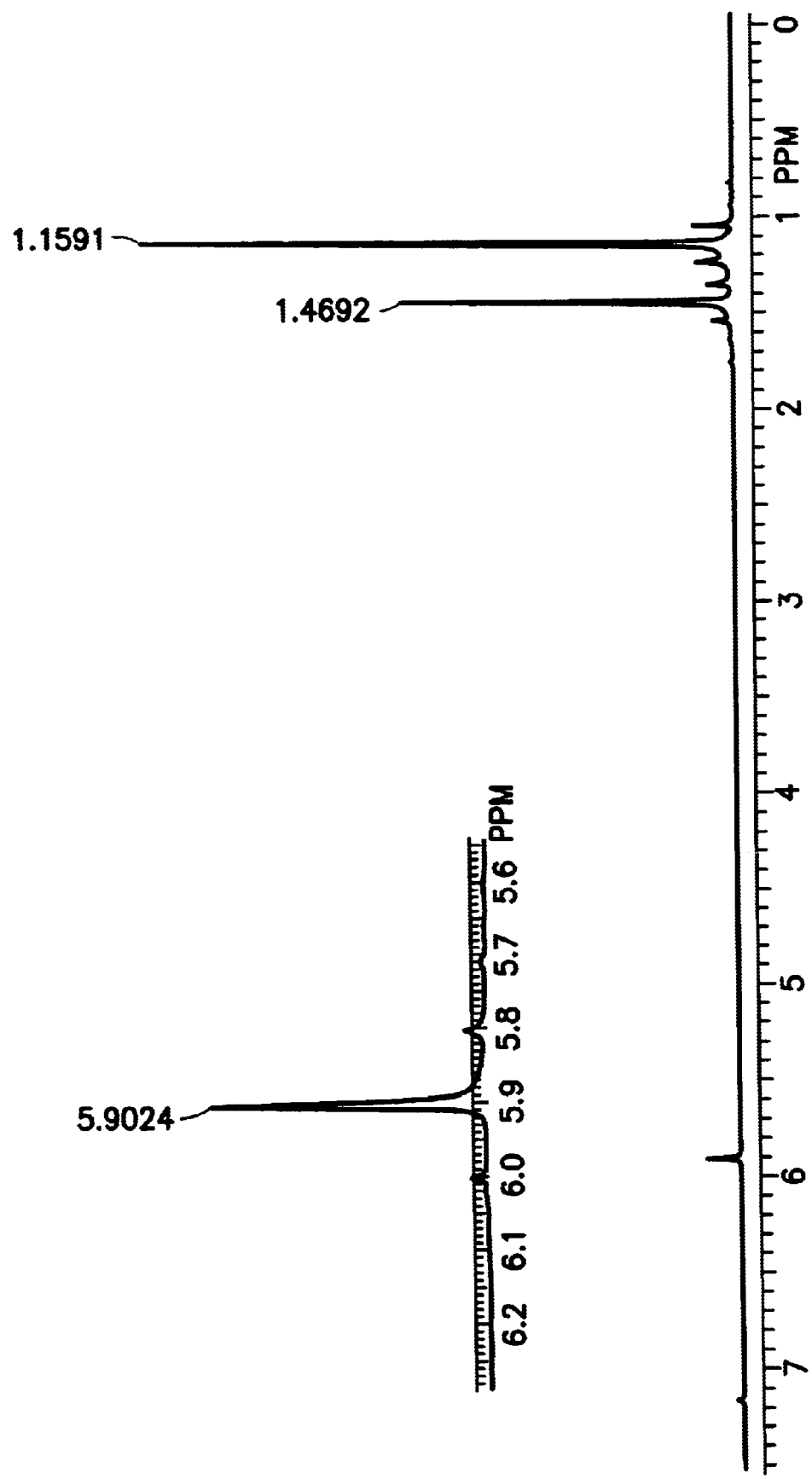
Figure 6C:
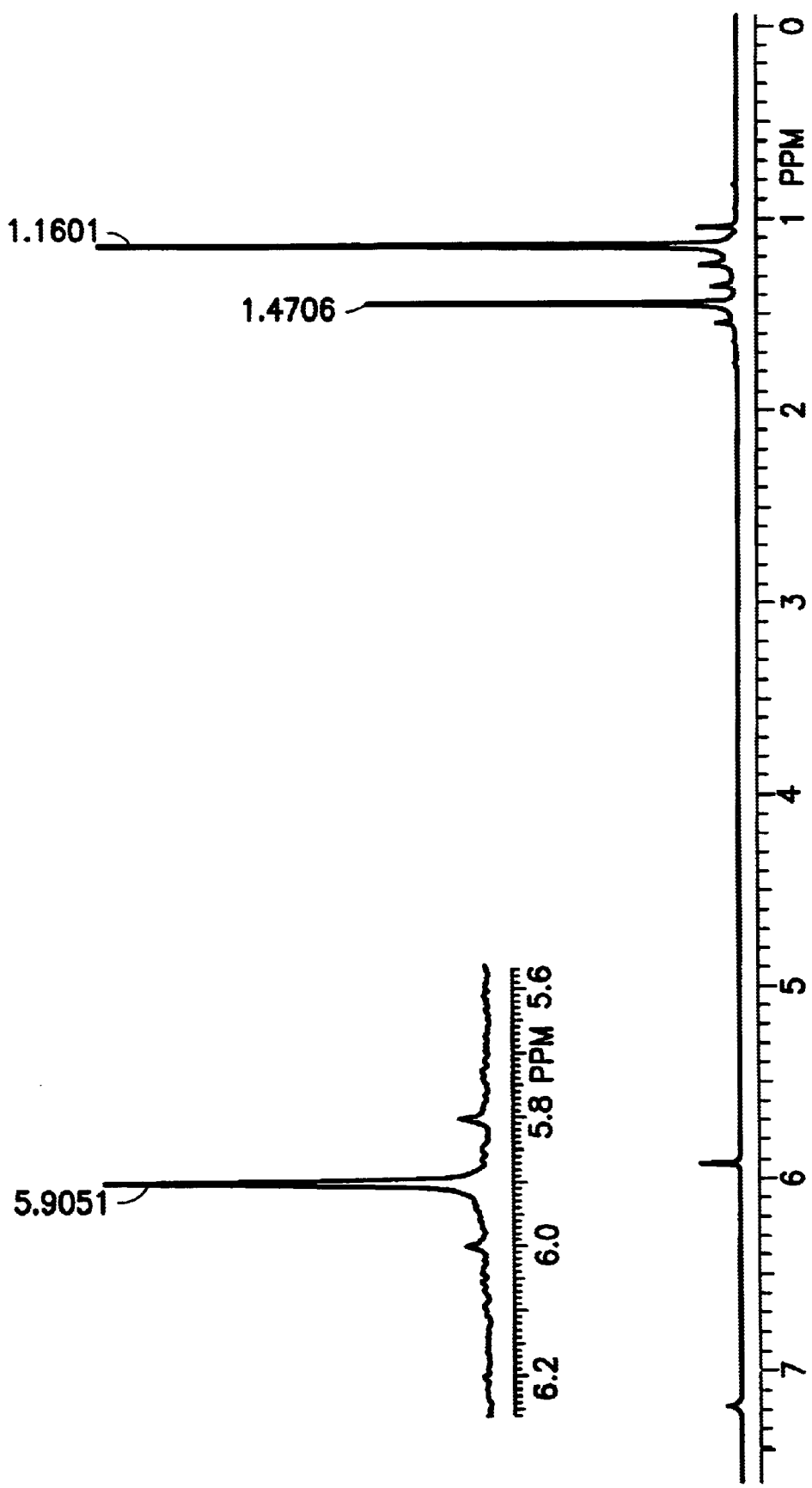
Figure 6D:
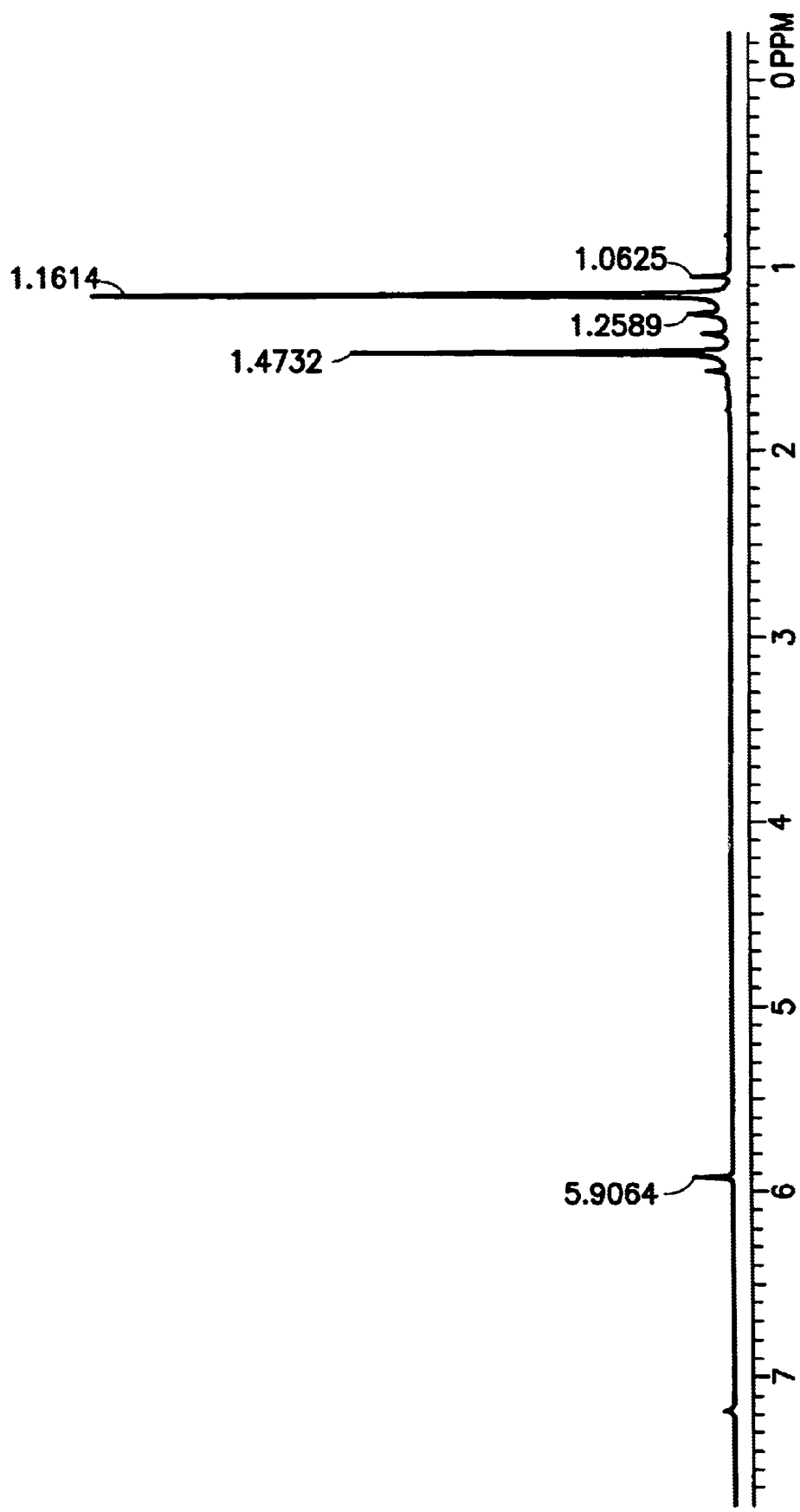

NMR Characterization of Zr(thd)$_2$(O-tBu)$_2$:

A sample of Zr(thd)$_2$(O-tBu)$_2$ is dissolved in deuterated benzene solvent. FIGS. 6a–6d, show the $^1$H NMR (C$_6$D$_6$), δ (ppm) spectra of a single sample of Zr(thd)$_2$(O-tBu)$_2$ over a period of approximately twentynine days. The original sample in FIG. 6a shows essentially all of the compound to be in the cis-phase 1.16 (s, 36H=4×—C(C$\underline{H}_3$)$_3$ of thd ligands) and 5.91 (s, 2H=2×C$\underline{H}$ of thd ligands). FIGS. 6b–6d support the finding that the presence of the bulky t-butyl groups in the alkoxide ligands limit the occurrence of cis- to trans-equilibration and eliminates the proportionation to dinuclear species over time, particularly when the compound is in an organic solution or suspension (FIG. 6b time lapse=3 days, FIG. 6c time lapse=13 days, FIG. 6d time lapse=29 days).

Synthesis and Characterization of Zr(thd)$_2$(O-tBu)$_2$:

The synthesis of Zr(thd)$_2$(O-tBu)$_2$ was carried out under a steady flow of N$_2$. A 250 mL Schlenk flask was charged with 10.0 g(~0.0261 moles) of freshly distilled Zr(O-tBu)$_4$ in 100 mL of dry toluene or pentane solvent. The temperature of the solvent, whether pentane or toluene, was held at a temperature between about 0° C. to 5° C.

Approximately two equivalents of Hthd in the amount of 9.55 g(~0.0582 moles) were slowly added into the Zr(O-tBu)$_4$ solution under constant stirring by a magnetic stirring bar.

After complete addition of Hthd into the Zr(O-tBu)$_4$ solution, the mixture was stirred for several hours. The solvent was then removed from the mixture under vacuum.

A white solid product was isolated, constituting Zr(thd)$_2$(O-tBu)$_2$ in an amount of 15.7 g(~0.0261 moles), as a near quantitative yield of solid Zr(thd)$_2$(O-tBu)$_2$.

The yielded white solid was analyzed using NMR. technique, wherein M.P.: 200° C.; $^1$H NMR (C$_6$D$_6$), δ (ppm), 5.90 (s, 2H=2×CH of did ligands), 1.47 (s, 18H=2×–OC(CH$_3$)$_3$ of tert-butaxide), 1.16 (s, 36H=4×–C(CH$_3$)$_3$ of thd ligands). See FIG. 6a. The protons of the t-butyl groups are magnetically equivalent at room temperature, indicating the presence of only cis-conformation within this molecule, in contrast, the Zr(thd)$_2$(O-iPr)$_2$ species displays the ability to form trans-conformer over time in solution, see for example FIGS. 4a–4c Therefore, the sterically bulky t-butyl groups limit the ability of the Zr(thd)$_2$(O-tBu)$_2$ molecule to undergo via- to tans-equilibration and later proportionation to the dinuclear species [Zr(thd)$_2$(O-tBu)$_2$]$_2$.

The Zr(thd)$_2$(O-tBu)$_2$ compound can be synthesized in high elemental purity as a result of the facile purification of Zr(O-tBu)$_4$ by distillation.

The present invention provides efficient high purity zirconium and/or hafnium precursors. The precursors of the invention enable zirconium- and/or hafnium-containing films to be readily formed, exhibiting good electrical properties and low current leakages.

Although the invention has been variously disclosed herein with reference to illustrative embodiments and features, it will be appreciated that the embodiments and features described hereinabove are not intended to limit the invention, and that other variations, modifications, and other embodiments will suggest themselves to those of ordinary skill in the art. The invention therefore is to be broadly construed, consistent with the claims hereafter set forth.

What is claimed is:

1. A CVD source reagent composition for forming a metal oxide thin film selected from the group consisting of gate dielectric, high dielectric constant and ferroelectric, said source reagent composition comprising a Hf metal precursor of the formula:

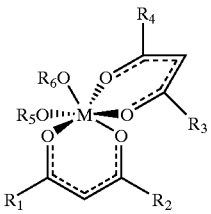

wherein:
M is Hf;
each of R$_1$, R$_2$, R$_3$, and R$_4$ is independently selected from the group consisting of H, aryl, perfluoroaryl, C$_1$–C$_8$ alkyl, and C$_1$–C$_8$ perfluoroalkyl; and
R$_5$ and R$_6$ are bath t-butyl groups.

2. The CVD source reagent composition of claim 1, wherein the Hf metal precursor comprises at least one β-diketonate moiety selected from the group consisting of 2,4-pentanedione (acac), 1,1,1-trifluoro-2,4-pentanedionato (tfac), 1,1,1,5,5,5-hexafluoro-2,4-pentanedionato (hfac), 2,2,6,6-tetramethyl-3,5-heptanedionato (thd) 2,2,7-trimethyl-3,5-octanedionato (tod), and 6,6,7,7,8,8,8-heptafluoro-2,2-dimethyl-3,5-octanedionato (fad).

3. The CVD source reagent composition of claim 1, wherein the Hf metal precursor comprises M(thd)$_2$(O-tBu)$_2$.

4. The CVD source reagent composition of claim 3, wherein M(thd)$_2$(O-tBu)$_2$ has been synthesized by a synthesis procedure including the following reaction:

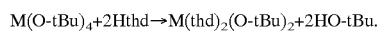

M(O-tBu)$_4$+2Hthd→M(thd)$_2$(O-tBu)$_2$+2HO-tBu.

5. The CVD source reagent composition of claim 4, wherein M(thd)$_2$(O-tBu)$_2$ has been synthesized by using a M(O-tBu)$_4$ solution comprising a solvent medium selected from the group consisting of aryl, hydrocarbon, and combinations thereof.

6. The CVD source reagent composition of claim 5, wherein the M(O-tBu)$_4$ solution comprises toluene.

7. The CVD source reagent composition of claim 5 wherein the M(O-tBu)$_4$ solution comprises pentane.

8. The CVD source reagent composition of claim 1 further comprising a solvent medium.

9. The CVD source reagent composition of claim 8, wherein the solvent medium comprises a solvent species selected from the group consisting of ethers, glymes, tetraglymes, amines, polyamines, aliphatic hydrocarbon solvents, aromatic hydrocarbon solvents, cyclic ethers, and compatible combinations of two or more of the foregoing.

10. The CVD source reagent composition of claim 8, Wherein the solvent medium comprises octane.

11. A method of forming a Hf metal oxide tin film selected from the group consisting of doped gate dielectric, high dielectric constant and ferroelectric, on a substrate, comprising the steps of:
vaporizing a source reagent composition comprising a Hf metal precursor to form a source reagent vapor;
transporting said source reagent vapor into a chemical vapor deposition zone, optionally using a carrier gas;
contacting the source reagent vapor with a substrate in said chemical vapor deposition zone in the presence of an oxidizer and at elevated temperature to deposit a Hf doped gate dielectric, high dielectric constant or ferroelectric metal oxide thin film on the substrate;

wherein said Hf metal precursor has a general formula of:

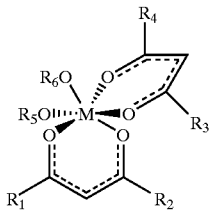

wherein M is Hf;

each of $R_1$, $R_2$, $R_3$, and $R_4$ is independently selected from the group consisting of H, aryl, perfluoroaryl, $C_1$–$C_8$ alkyl, and $C_1$–$C_8$ perfluoroalkyl; and $R_5$ and $R_6$ are both t-butyl groups.

12. The method of claim 11, wherein the Hf metal precursor comprises a β-diketonate moiety selected from the group consisting of 2,4-pentanedione (acac), 1,1,1-trifluoro-2,4-pentanedionato (tfac), 1,1,1,5,5,5-hexafluoro-2,4-pentanedionato (hfac), 2,2,6,6-tetramethyl-3,5-heptanedionato (thd), 2,2,7-trimethyl-3,5-octanedionato (tad), and 6,6,7,7,8,8,8-heptafluoro-2,2-dimethyl-3,5-octanedionato (fod).

13. The method of claim 11, wherein the Hf metal precursor comprises $M(thd)_2(O\text{-}tBu)_2$.

14. The method of claim 13 wherein $M(thd)_2(Q\text{-}tBu)_2$ has been synthesized by a procedure including the following reaction:

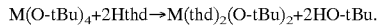

15. The method of claim 14, wherein $M(thd)_2(O\text{-}tBu)_2$ has been synthesized using a solution comprising a solvent medium selected from the group consisting of aryl and hydrocarbon.

16. The method of claim 15, wherein the $M(O\text{-}tBu)_4$ solution comprises toluene.

17. The method of claim 15, wherein the $M(O\text{-}tBu)_4$ solution comprises pentane.

18. The method of claim 14, wherein the source reagent composition further comprises a solvent medium.

19. The method of claim 18, wherein the solvent medium comprises a solvent species selected from the group consisting of ethers, glymes, tetraglymes, amines, polyamines, aliphatic hydrocarbon solvents, aromatic hydrocarbon solvents, cyclic ethers, and compatible combinations of two or more of the foregoing.

20. The method of claim 18, wherein the solvent medium is octane.

21. The method of claim 19, wherein the step of vaporizing the source reagent composition is carried out at a vaporization temperature in a range from about 100° C. to about 300° C.

22. The method of claim 11, wherein a carrier gas is used for transporting the source reagent vapor and said carrier gas comprises argon.

23. The method of claim 11, wherein the oxidizer comprises oxygen.

24. The method of claim 11, wherein the Hf doped gate dielectric or high dielectric constant metal oxide thin film is deposited on the substrate at a deposition temperature in a range of from about 350° C. to about 750° C.

25. A CVD source reagent composition comprising a Zr/Hf metal precursor of the formula:

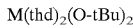

wherein:

M is Zr or Hf; and the Zr/Hf metal precursor has been synthesized by reacting $M(O\text{-}tBu)_4$ with two equivalents of Hthd in a solution comprising a dry hydrocarbon solvent under an inert gas flow according to the following reaction;

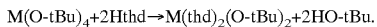

26. The CVD source reagent composition of claim 25, wherein M is Zr.

27. The CVD source reagent composition of claim 25, wherein M is Hf.

28. The CVD source reagent composition of claim 25 wherein the $M(O\text{-}tBu)_4$ solution comprises toluene.

29. The CVD source reagent composition of claim 25, wherein the $M(O\text{-}tBu)_4$ solution comprises pentane.

30. The CVD source reagent composition of claim 25, further comprising a solvent medium.

31. The CVD source reagent composition of claim 30, wherein the solvent medium comprises a solvent species selected from the group consisting of ethers, glymes, tetraglymes, amines, polyamines, aliphatic hydrocarbon solvents, aromatic hydrocarbon solvents, cyclic ethers, and compatible combinations of two or more of the foregoing.

32. The CVD source reagent composition of claim 30, wherein the solvent medium composes octane.

33. A method of forming a Zr/Hf metal oxide thin film selected from the group consisting of doped gate dielectric, high dielectric constant and ferroelectric, on a substrate, comprising the steps of:

vaporizing a source reagent composition comprising a Zr/Hf metal precursor to form a source reagent vapor;

transporting said source reagent vapor into a chemical vapor deposition zone, optionally using a carrier gas;

contacting the source reagent vapor with a substrate in said chemical vapor deposition zone in the presence of an oxidizer and at elevated temperature to deposit a Zr/Hf doped gate dielectric, high dielectric constant or ferroelectric metal oxide thin film on the substrate;

wherein said Zr/Hf metal precursor has a formula of:

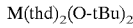

wherein M is Zr or Hf; and the Zr/Hf metal precursor has been synthesized by reacting $M(O\text{-}tBu)_4$ with two equivalents of Hthd in a solution comprising a dry hydrocarbon solvent under an inert gas flow according to the following reaction;

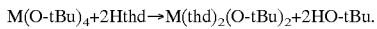

34. The method of claim 33, wherein M is Zr.

35. The method of claim 33, wherein M is Hf.

36. The method of claim 33, wherein $M(thd)_2(O\text{-}tBu)_2$ has been synthesized using a $M(O\text{-}tBu)_4$ solution comprising a solvent medium selected from the group consisting of aryl and hydrocarbon.

37. The method of claim 36, wherein the $M(O\text{-}tBu)_4$ solution comprises toluene.

38. The method of claim 36, wherein the $M(O\text{-}tBu)_4$ solution comprises pentane.

39. The method of claim 33, wherein the source reagent composition further comprises a solvent medium.

40. The method of claim 39, wherein the solvent medium comprises a solvent species selected from the group consisting of ethers, glymes, tetraglymes, amines, polyamines, aliphatic hydrocarbon solvents, aromatic hydrocarbon solvents, cyclic ethers, and compatible combinations of two or more of the foregoing.

41. The method of claim 39, wherein the solvent medium is octane.

42. The method of claim 33, wherein the step of vaporizing the source reagent composition is carried out at a vaporization temperature in a range from about 100° C. to about 300° C.

43. The method of claim 33, wherein a carrier gas is used for transporting the source reagent vapor and said carrier gas comprises argon.

44. The method of claim 33, wherein the oxidizer comprises oxygen.

45. The method of claim 33, wherein the Zr/Hf doped gate dielectric or high dielectric constant metal oxide thin film is deposited on the substrate at a deposition temperature in a range of from about 350° C. to about 750° C.

* * * * *